United States Patent [19]

Shearing

[11] 4,159,546

[45] Jul. 3, 1979

[54] INTRAOCULAR LENS

[76] Inventor: Steven P. Shearing, 2320 S. Rancho Dr., #103, Las Vegas, Nev. 89102

[21] Appl. No.: 806,957

[22] Filed: Jun. 15, 1977

[51] Int. Cl.² .............................. A61F 1/16; A61F 1/24
[52] U.S. Cl. .......................................................... 3/13
[58] Field of Search ........................................ 3/13, 1

[56] References Cited

U.S. PATENT DOCUMENTS

| | | | |
|---|---|---|---|
| 3,906,551 | 9/1975 | Otter | 3/13 |
| 3,925,825 | 12/1975 | Richards et al. | 3/13 |
| 4,014,049 | 3/1977 | Richards et al. | 3/13 |
| 4,080,709 | 3/1978 | Poler | 3/13 X |

OTHER PUBLICATIONS

Intraocular Lenses and Implants (book) by Peter Choyce, London, H. K. Lewis & Co., Ltd., 1964, pp. 13-15.

*Primary Examiner*—Ronald L. Frinks
*Attorney, Agent, or Firm*—Seiler & Quirk

[57] ABSTRACT

An improved intraocular lens comprises a plastic lens body and a plurality of flexible and memory retaining non-biodegradable strands, each strand having one end secured to the lens body and the opposite end unsecured. Preferably, the strands are composed of polypropylene. In cataract surgery, following either intra or extra capsular extraction, the lens of the invention is implanted in the posterior chamber.

4 Claims, 10 Drawing Figures

INTRAOCULAR LENS

BACKGROUND OF THE INVENTION

In cataract surgery, following either intracapsular or extracapsular extraction of the cataractous lens, an intraocular lens may be implanted. Various types of such lenses have been proposed. They may be implanted in the anterior chamber, the posterior chamber, or in the pupilary space. In anterior chamber placement, the lens is fixed, anchored or supported in the angle at the intersection of the cornea and the iris. Although the anterior chamber is the most readily accessible for such lens implantation, unless the lens is carefully sized or fitted to precisely be supported across the angle, it may traumatize the cornea, or angle structures. A pupilary space lens is supported by the iris, and commonly is secured directly to the iris. Although such a lens is centered in the pupil or pupilary space, the support may be poor and the iris may not be dilated when desired. The posterior chamber may be considered to be most advantageous for intraocular lens implantation because of the original lens being located in that chamber. However, it is the most difficult and least accessible area for such implantation and fixation, expecially following intracapsular extraction.

SUMMARY OF THE INVENTION

It is to the elimination of the aforesaid problems that the intraocular lens of the present invention is directed. The lens incorporates a plurality of non-biodegradable strands which are fixed to the lens body, and which strands are composed of a material which is flexible and yet has specific spring-like memory qualities whereby the strands may be substantially fully compressed or offset from the normal rest position and thereafter returned to the fully extended condition when pressure is removed. Such a feature is achieved by securing only one strand to the lens with the opposite end being unsecured. The lens is readily inserted into the posterior chamber and fixed on the ciliary body or muscle and automatically centered with respect to the pupil. These features of the lens as well as its implantation will be more fully explained in the following detailed disclosure.

DETAILED DESCRIPTION OF THE INVENTION

Figure 1:
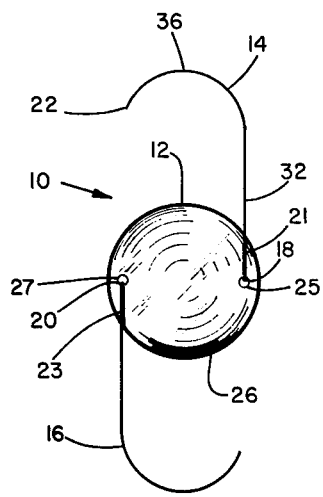
FIG. 1 is a front elevational view of the intraocular lens of the invention.

In FIG. 1 is shown the intraocular lens 10 of the invention having a lens body 12 and a pair of strands 14 and 16, which strands support the lens body when it has been implanted. The lens body 12 may be produced from any suitable material, preferably a plastic which is non-degradable and non-toxic in the eye. A preferred composition for the lens body comprises an acrylic resin which has been manufactured to a desired prescription and which has a desirable shape. The most preferred lens body composition comprises polymethyl methacrylate, and preferably an ophthalmic grade polymer having a very low free or residual monomer.

Figure 2:
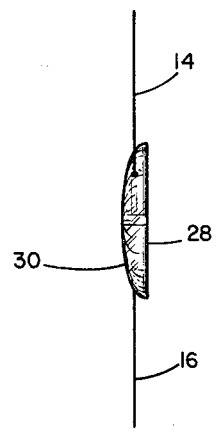
FIG. 2 is a side elevational view thereof.

A preferred shape of the lens body is illustrated in FIGS. 1 and 2, in which the anterior lens body surface 30 is convex while the posterior surface 28 is flat or planar. The lens body peripheral edge 26 is shown to be circular which is the preferred lens shape, although any other desirable lens body surface and edge shapes may be used, and those shown are by way of illustration only.

Once implanted, the lens body is supported and held in place by a plurality of support strands. In the preferred embodiment shown, two of such strands 14 and 16 are used, each one being attached or secured adjacent to the peripheral lens body edge and on opposite sides thereof. These strands must be flexible, that is they must be yielding under pressure, but must also have a memory retaining feature whereby the strand will return to its normal extended position or will automatically tend to do so once the pressure has been released. Thus, the strands must have a spring-like quality as will be further explained hereinafter.

The strands are attached to the lens body by any convenient or desirable means. Especially useful is means for securing the strands to the lens body adjacent the peripheral lens body edge so as to have minimum interference with the lens body itself. This is conveniently achieved by providing bored, drilled or molded shafts 21 and 23 along the sides of the lens body and inserting one end of each of the strands into a shaft. The inserted strand end may then be secured by adhesive or other mechanical means. However, an especially convenient means for securing the strand end comprises providing an orifice 25 and 27 through the lens body and across each shaft 21 and 23 respectively. In other words, each orifice intersects a shaft conveniently at an angle approximately normal to the elongated shaft axis. When one end has been inserted into a shaft and is exposed to the orifice, a heated plunger or needle is placed in the orifice thereby melting the strand end whereby an enlarged end portion is formed which has a size greater than the cross-section of the shaft. This will prevent the strand from being removed or pulled from the shaft. Alternatively, both the strand end and acrylic material within the orifice may become molten thereby uniting to provide an extensive bond therebetween to prevent removal of the strand. Again, however, any convenient means such as adhesive or the like may be used to so secure the strand.

Figure 3:
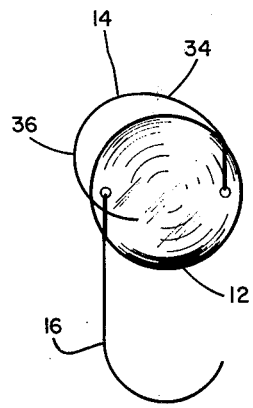
FIG. 3 is a front elevational view of the lens of FIG. 1 illustrating support strand compression.
Figure 8:
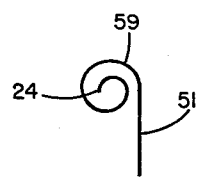
FIG. 8 illustrates an alternative lens support strand shape.

Observing further the strands 14 and 16 of FIGS. 1-3, each one has a substantially straight leg or portion 32 extending away from the lens body, and a curved or arched portion 36, terminating in an end 22. The purpose for the arched portion is to present a rounded strand surface for being urged against or abutting the ciliary body or muscle when the lens is implanted in the posterior chamber. Further, end 22 of the strand is directed back toward the lens body as shown. This feature is intended to prevent the strand end from being pointed or jabbed against the delicate tissue within the eye during and after implantation. For this purpose, end 22 preferably extends in a direction or along a plane forming an acute angle with the direction of straight strand leg or portion 32. In other words, if the plane, along which direction unsecured strand end 22 lies, is extended to meet the directional plane along which straight strand portion 32 extends, an acute angle will be formed therebetween. Generally, the smaller the angle, the more unsecured end 22 will be directed toward the lens body, and concomitantly, the less will be the open exposure of that unsecured strand end and the less likely will be the possibility of its causing injury during or after the implant operation. Moreover, the unsecured strand end may even be directed back toward the straight strand end portion 32 or it may even be further curved as illustrated in FIG. 8. That embodiment illustrates an unsecured strand end 24 terminating within an arch portion 59 on strand 51, which further illustrates a modification whereby the strand end is formed to prevent undue exposure of the unsecured strand end. The length of the arched strand portion 36 is not so critical, again it being understood that the purpose therefor is to provide a rounded strand surface to contact the eye tissue once the lens is implanted. The longer and more gradual the arch, the less likely there will be any injury or trauma to the ciliary body tissue against which the arched strand portion abuts. Thus, the actual shape of the arched strand portion is not so critical, nor is the shape of the strand between the lens body and the arch or the arch and the unsecured strand end, so long as the spring-like and memory retaining qualities of the strand are not impaired nor is the free or unsecured strand end overexposed for the reasons previously described.

FIG. 3 illustrates the lens of the invention with supporting strand 14 being illustrated in a position as it might be forced under pressure. Under such pressure, otherwise normally straight strand leg or portion 34 has been bent so that the strand arched portion 36 lies relatively close to the lens body 12. The relationship of the strand when not being forced out of its rest position by pressure is illustrated by observing strand 16. Thus, the criticality of the flexibility and yet memory retention of the spring-like support strand is to be noted. A most suitable strand material to achieve such a feature, and used in the lens device of the invention, comprises polypropylene. A most preferred strand composition is a proprietary FDA approved polypropylene Ethicon brand "Prolene," supplied by Ethicon Pharmaceutical Company. Such material has superior qualities over other strand materials such as gut, silk and nylon. The former materials, although flexible, do not achieve the necessary or desired spring-like memory retention qualities necessary, and nylon can not be flexed enough under minor pressures as well as its being heavier than polypropylene and causing potential reactions within the eye after implantation. Moreover, these inferior materials are subject to losing their resilience or necessary spring retention whereby lens centering in the pupil would be lost and requiring removal and further implant surgery.

Figure 4:
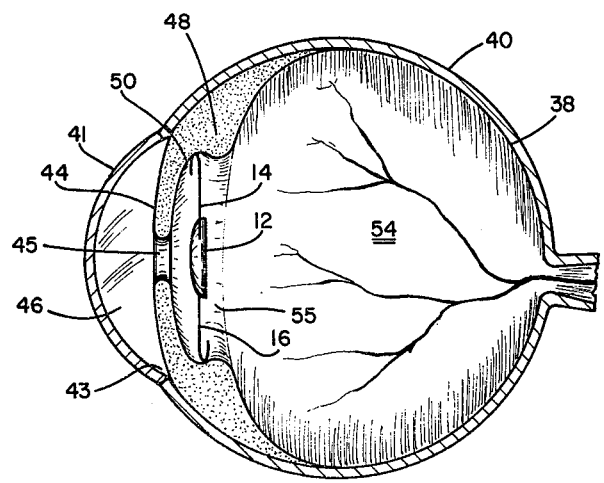
FIG. 4 is a cross-section schematic of the human eye illustrating posterior chamber implantation of the lens of FIG. 1.

In FIGS. 4-7, there is illustrated the lens device of the present invention as it is inserted in the posterior chamber and fixed therein. In FIG. 4, the intraocular lens of the invention is shown located in the posterior chamber 55 and with its proximity to anterior chamber 46 and vitreous chamber 54 within eye 40. The vitreous chamber is surrounded by retina 38. Further, the implanted lens observed illustrates lens body 12 being centered with respect to pupil 45 defined by iris 44 and following an intracapsular extraction in which the entire lens including the lens capsule has been removed. It will observed that lens body 12 is supported by strands 14 and 16 which extend to and are urged against ciliary body or muscle 48 in the saddle 50 which extends therearound. In such a position, the lens body will be observed not to exert pressure against cornea 41 as it would if implanted in the anterior chamber 46 and fixed in the angle 43 thereof.

Figure 5:
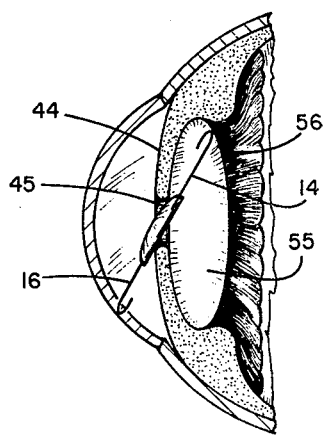
FIGS. 5-7 illustrate the stages of posterior chamber implantation of the lens of the invention.
Figure 6:
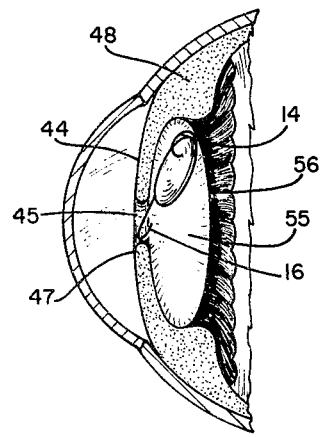
Figure 7:
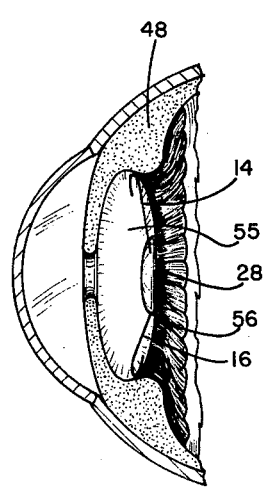

Observing also FIGS. 5-7, the procedural steps in implanting the lens of the invention in the posterior chamber may be observed following an extracapsular extraction in which the posterior capsule portion 56 remains. It will be understood that the additional advantage of such an extraction in leaving the capsule will allow potential capsular fixation of the lens in addition to the primary ciliary body fixation as previously described. In FIG. 5, the lens is being inserted through the pupil or pupilary cavity 45, with first or inferior strand 14 having entered the posterior chamber 55. As the procedure continues, the surgeon directs the lens further into the posterior chamber with strand 14 being compressed against ciliary body 48 whereby the spring-like strand is bent under the continued pressure much like the position illustrated in FIG. 3. This directional urging of the lens is continued until superior or second strand 16 has cleared the lower lip 47 of iris 44 as illustrated in FIG. 6. Thereafter, as viewed in FIG. 7, the spring-like strand 14 is allowed to expand as the pressure against that support member is released and the lens is allowed to become centered in posterior chamber 55. As this occurs, second strand 16 is urged downwardly until it is forced against the lower surface of the ciliary body. The posterior lens surface 28 is further shown as being fixed or supported by capsule 56. Accordingly, in such a position, the intraocular lens has achieved a superior support and fixation utilizing the lens and the technique of the invention.

The size of the lens device may be varied, with the lens body having a diameter of between about 4 and about 7 millimeters and preferably between about 5 and about 6 millimeters. The total length of the lens between the outermost extremities of the strands is between about 10 and about 15 millimeters and preferably between about 12 and about 13 millimeters. The important feature of the length of the lens, i.e. the extreme distance between the fully extended strands as illustrated in FIG. 1, is that such a distance is slightly larger than the ciliary space in which the lens is fixed in the posterior chamber. Thus, if the distance across the ciliary space is 12 millimeters, the preferred lens length will be about 13 millimeters, whereby, because of the spring-like qualities of the strands which continually are urged to their greatest extension, the strands will be slightly compressed on their fully extended position and thereby maintain the lens body correctly centered within the ciliary space and posterior chamber and with regard to the pupilary space. In other words, with such a lens length and ciliary space relationship, the spring-like strands will be biased and urged against the ciliary body to achieve this desired centering and fixation.

Figure 9:
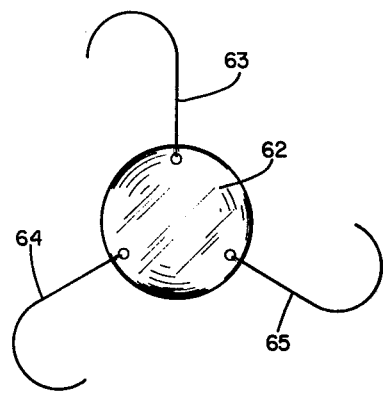
FIG. 9 illustrates a three strand embodiment of the lens of the invention.

Although two point fixation has been illustrated in the drawings with regard to the two strand device illustrated in FIGS. 1-3, alternatively, three or more strands may be provided to give three or more point fixation within the posterior chamber, using substantially the same procedure described herein. Such a lens is illustrated in FIG. 9 wherein three strands 63, 64 and 65 are spaced uniformly and secured adjacent the lens body peripheral edge as previously described. If such a lens is used, a three point fixation will be achieved once the lens is implanted, which may provide even more sufficient centering and fixation, although implantation procedure may be more difficult because of the additional strand. The same would hold true for a four strand embodiment as will be clearly understood within the purview of the invention herein. However, regardless of the number of strands utilized in achieving the lens described herein, the means for securing one end thereof may be like that previously described. Moreover, the necessity of having the other strand end unsecured or free is most important, because without such a feature, the spring-like feature of the memory retaining polypropylene composition strand would be affected. Thus, since full compression of at least one of the strands during implantation is essential according to the procedure described herein, if significant resistance of such compression were met, it would be disadvantageous. On the other hand, with one strand end unsecured or free, compression of the strand is readily achieved since it occurs by simple causing the single strand to bend from its normal straight position.

Figure 10:
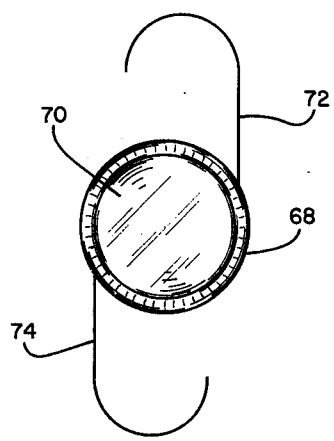
FIG. 10 shows a unitary ring and strand member in which the lens is held.

FIG. 10 illustrates an alternative lens embodiment in which lens body 70 is secured in a ring member 68 having attached thereto the supporting strands 72 and 74. The ring preferably comprises the same FDA approved polypropylene, previously described. With the strands also being of the same material, the ring and strands form a unitary member, which may be conveniently produced by a single molding operation. Alternatively, the polypropylene strands may be separately formed and welded or otherwise adhered to the ring. The ring member preferably will include a circular cavity exposed along the inner ring surface in which the lens body edge is secured. Where the polypropylene ring is somewhat flexible, the more rigid lens body may be conveniently snapped into such a ring cavity during assembly. The lens of this embodiment will be implanted using the same technique previously described. Other advantages and features as well as modifications of the intraocular lens and implantation procedure described herein and within the purview of the invention will be evident to those skilled in the art.

I claim:

1. In a cataract surgery following capsular extraction, a method of implanting an intraocular lens having an acrylic resin lens body and first and second flexible and memory retaining curved looped strands wherein one end of each strand is secured adjacent the peripheral edge of said lens body and the other end is unsecured, comprising inserting said lens through the pupil with said first strand first followed by said lens body, directing said first strand against the ciliary body, further urging said lens through the pupil thereby compressing said first strand until said second strand passes through said pupil, and directing said second strand against the ciliary body opposite said first strand, whereby the entire lens is located within the posterior chamber and posterior to the iris.

2. In cataract surgery following capsular extraction, a method of implanting an intraocular lens having a plastic lens body and first and second flexible and memory retaining curved looped strands wherein one end of each strand is secured adjacent the peripheral edge of said lens body and the other end is unsecured, comprising inserting said lens through the pupil with said first strand first followed by said lens body, directing said first strand into the posterior chamber, further urging said lens through the pupil and into the posterior chamber thereby compressing said first strand within the posterior chamber until said second strand passes through said pupil and into the posterior chamber, and directing said second strand opposite said first strand in the posterior chamber, whereby the entire lens is located and fixed within the posterior chamber and posterior to the iris.

3. The method of claim 2 wherein said capsular extraction is an extracapsular extraction in which at least a portion of the capsule remains in the posterior chamber and whereby said lens is inserted into said posterior chamber and fixed by the capsule therein.

4. In cataract surgery following capsular extraction, a method of implanting an intraocular lens having a plastic lens body and a plurality of flexible and memory retaining curved looped strands wherein one end of each strand is secured adjacent the peripheral edge of said lens body and the other end is unsecured, comprising inserting said lens through the pupil with a first one of said strands first following by said lens body, directing said first strand into the posterior chamber, and further urging said lens through the pupil and into the posterior chamber thereby compressing said first strand within the posterior chamber until the other of said strands pass through said pupil and directing said other strands into the posterior chamber, whereby the entire lens is located and fixed within the posterior chamber and posterior to the iris.

* * * * *